United States Patent
Davidson et al.

(10) Patent No.: US 9,868,945 B2
(45) Date of Patent: Jan. 16, 2018

(54) LINKING METHODS, COMPOSITIONS, SYSTEMS, KITS AND APPARATUSES

(75) Inventors: John Davidson, Guilford, CT (US); Theo Nikiforov, Carlsbad, CA (US); Guobin Luo, Oceanside, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 13/984,346

(22) PCT Filed: Feb. 8, 2012

(86) PCT No.: PCT/US2012/024266
§ 371 (c)(1),
(2), (4) Date: Sep. 13, 2013

(87) PCT Pub. No.: WO2012/109315
PCT Pub. Date: Aug. 16, 2012

(65) Prior Publication Data
US 2013/0344561 A1    Dec. 26, 2013

Related U.S. Application Data

(60) Provisional application No. 61/440,723, filed on Feb. 8, 2011.

(51) Int. Cl.
*C12N 11/10* (2006.01)
*C12N 9/12* (2006.01)
*C12Q 1/68* (2006.01)

(52) U.S. Cl.
CPC .......... *C12N 11/10* (2013.01); *C12N 9/1241* (2013.01); *C12Q 1/68* (2013.01); *G01N 2333/9126* (2013.01)

(58) Field of Classification Search
CPC .............. C12N 11/10; C12N 9/1241
(Continued)

(56) References Cited

U.S. PATENT DOCUMENTS 5,652,107 A    7/1997  Lizardi et al.
5,874,282 A *  2/1999  Riggs ................... C12N 9/1252
                                                      435/194
(Continued)

FOREIGN PATENT DOCUMENTS

WO    WO-98/25146    6/1998
WO    WO-02/04680    1/2002
(Continued)

OTHER PUBLICATIONS

Lundblad (2005). Chemical Reagents for Protein Modification, 3rd Ed., ISBN: 0-8493-1983-8, 311 pages.*
(Continued)

*Primary Examiner* — Sean C Barron

(57) ABSTRACT

In some embodiments, the disclosure relates generally to methods as well as related compositions, systems, kits and apparatus comprising linking proteins to target compounds and/or to locations of interest using tethers. For example, the tether can be used to link the protein to a target compound, for example, to link an enzyme to a substrate. Similarly, the tether can be used to link the protein at or near a desired location on a surface. In one group of embodiments, the tether includes a polynucleotide and the target compound or location on the surface includes another polynucleotide that is capable of hybridizing to the tether. In such embodiments, the tether can be used to link the protein to the target compound or location using nucleic acid hybridization.

15 Claims, 13 Drawing Sheets

Tethered polymerase survives high salt washes and produces key signal

- Tethered Ion Sequencing Pol result >800k Q17 reads, key signal>30

Robust key signal

(58) Field of Classification Search
USPC .......................................................... 435/178
See application file for complete search history.

(56) References Cited

U.S. PATENT DOCUMENTS

| | | | |
|---|---|---|---|
| 2002/0058278 A1* | 5/2002 | Stefano et al. ................... | 435/6 |
| 2005/0042633 A1 | 2/2005 | Williams | |
| 2007/0172866 A1* | 7/2007 | Hardin et al. .................... | 435/6 |
| 2009/0298088 A1* | 12/2009 | Belyaev et al. ................ | 435/7.1 |
| 2010/0260465 A1 | 10/2010 | Hanzel et al. | |
| 2015/0086994 A1 | 3/2015 | Williams et al. | |

FOREIGN PATENT DOCUMENTS

| | | |
|---|---|---|
| WO | WO-2005/094441 | 10/2005 |
| WO | WO-2010/016937 | 2/2010 |

OTHER PUBLICATIONS

Liapakis et al. (1999). The substituted-cysteine accessibility method (SCAM) to elucidate membrane protein structure. Current Protocols in Neuroscience, supplement 8, p. 4.15.1-4.15.10.*
Boileau et al. (1999). Mapping the agonist binding site of the GABA-A receptor: evidence for a beta strand. Journal of Neuroscience, v19(12), p. 4847-4854.*
Barron et al. (2009). An Allosteric Modulator of alpha7 Nicotinic Receptors, N-(5-Chloro-2,4-dimethoxyphenyl)-N'-(5-methyl-3-isoxazolyl)-urea (PNU-120596), Causes Conformational Changes in the Extracellular Ligand Binding Domain Similar to Those Caused by Acetylcholine. Molecular Pharamcology,v76(2), p. 253-263.*
Zhang et al. (2009). Agonist and antagonist-induced conformational changes of loop F and their contributions to the rho-1 GABA receptor function. Journal of Physiology, v587(1), p. 139-153.*
Dijk et al. (2009). Synthesis and applications of biomedical and pharmaceutical polymers via click chemistry methodolgies. Bioconjugate Chemistry, v20(11), p. 2001-2016.*
Hastrup et al. (2003). The human dopamine transporter forms a tetramer in the plasma membrane. JBC, v278(46), p. 45045-45048.*
Pearson et al. (2007). Reversible photoregulation of binding of alpha-chymotrypsin to a gold surface. JACS, v129, p. 14862-14863.*
Pavlov et al. (epub 2009). DNA polymerases at the eukaryotic fork—20 years later. Mutation Research, v685, p. 45-53.*
Burke (2003). Ribozyme-Catalyzed Genetics, Madam Curie Bioscience Database [Internet], 27 pages + appended snapshot for most recent update of the article.*
Li et al. (1987). Enzyme-linked synthetic oligonucleotide probes: non-radioactive detection of enterotoxigenic *Escherichia coli* in faecal specimens. Nucleic Acids Reseaerch, v15(13), p. 5275-5287.*
Fernley et al. (1968). Studies on Alkaline Phosphatase: Phosphorylation of Calf-Intestinal Alkaline Phosphatase by 32P-Labelled Pyrophosphate. Biochem J, v107, p. 279-283.*
Wilchek et al. (1979). Haloacetyl Derivatives. Methods in Enzymology, v46, p. 153-157.*
Ishii et al. (1993). Bead-Based Sandwich Hybridization Characteristics of Oligonucleotide-Alkaline Phosphatase Conjugates and Their Potential for Quantitating Target RNA Sequences. Bioconjugate Chem, v4, p. 34-41.*
Ebersole et al. (1990). Spontaneously Formed Functionally Active Avidin Monolayers on Metal Surfaces: A Strategy for Immobilizing Biological Reagents and Design of Piezoelectric Biosensors. J Am Chem Soc, v112, p. 3239-3241.*
Champoux (1977). Strand breakage by the DNA untwisting enzyme results in covalent attachment of the enzyme to DNA. PNAS, v74(9), p. 3800-3804.*
Tse et al. (1980). Covalent Bonds between Protein and DNA. JBC, v255(12), p. 5560-5565.*
DeMott et al. (2002). Covalent Trapping of Human DNA Polymerase beta by the Oxidative DNA Lesion 2-Deoxyribonolactone. JBC, v277(10), p. 7637-7640.*
Perry (1999). Solid-Phase Sequencing of Biotinylated PCR Products with Streptavidin-Coated Magnetic Beads. Methods in Molecular Medicine, v31, p. 49-54.*
Fixe et al. Functionalization of poly(methyl methacrylate)(PMMA) as a substrate for DNA microarrays. Nucleic Acids Research, 2004, vol. 32, No. 1 e9, 8 pages.*
Hamels et al. A PCR-microarray method for the screening of genetically modified organisms. Eur Food Res Technol (2009), v228, p. 531-541.*
D. Cojocari. "Twenty One Amino Acids" (2010, 1 page).*
Liu et al. DNA hybridization on silica microbeads that are physically adsorbed as arrays on glass surfaces. Analytica Chimica Acta (2006), v562, p. 1-8.*
PCT/US2012/024266, International Search Report and Written Opinion dated May 25, 2012, 1-14.

\* cited by examiner

Bst Large Fragment (1L3U) conjugated to FAM labeled oligo

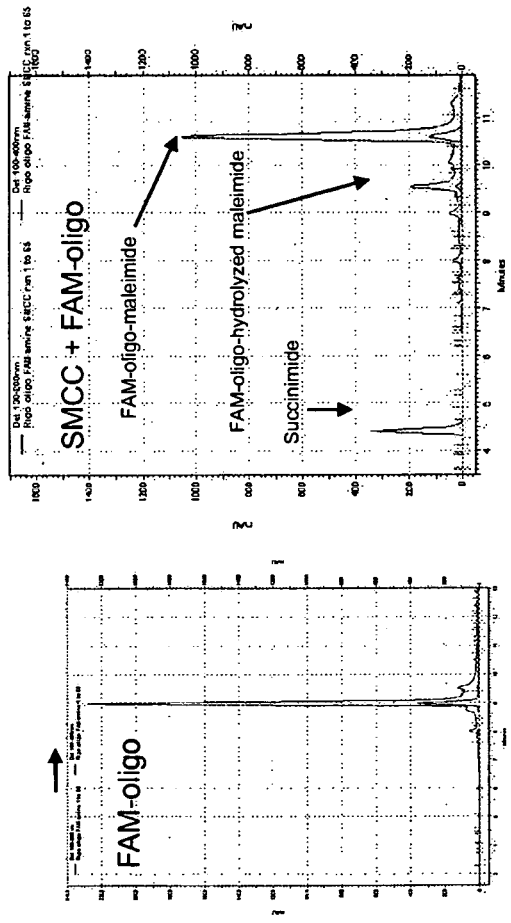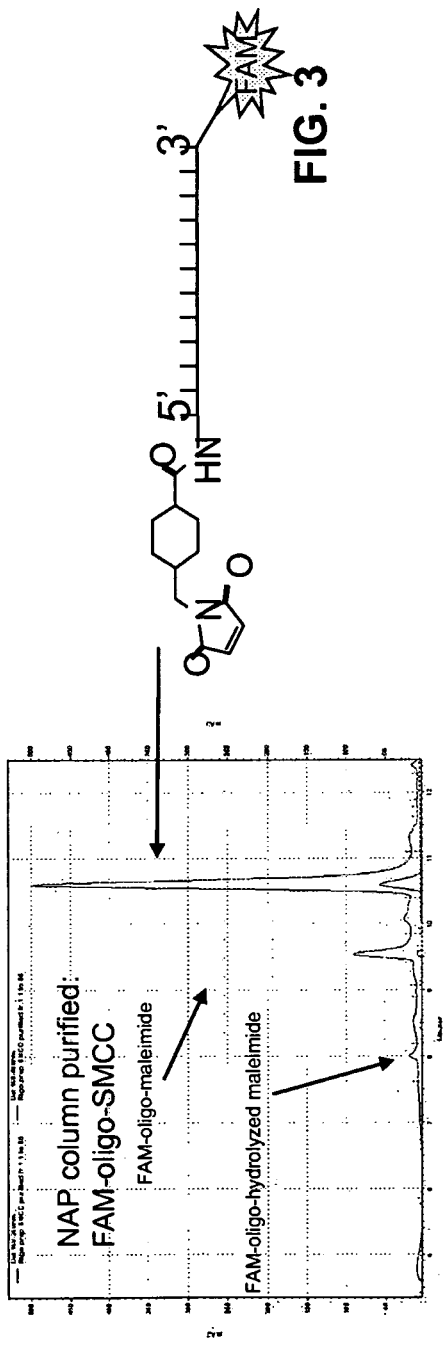
FIG. 3

FIG. 8  Oligo tethering reaction results: NaCl pushed reaction yield to greater than 50%

FAM-oligo-maleimide dissolved in 50 mM ACES pH 6.8, 2 mM EDTA

| RXN | Bst (41.6 µM) | FAMoligo-maleimide (264 µM) | NaCl (5M) | Buffer added for gel |
|---|---|---|---|---|
| RP12092010R5 | 1 µL | 24 µL | 0 µL | 2.5 µL |
| RP12092010R6 | 1 µL | 24 µL | 2.5 µL | 0 µL |
| RP12092010R7 | 1 µL | 24 µL | 5 µL | 24 µL |
| RP12092010R8 | 1 µL | 48 µL | 5 µL | 0 |
| Bst (1) | 1 µL | 0 µL | | 26.5 µL |
| Bst (2) | 1 µL | 0 µL | | 53 µL |

High salt washes off untethered polymerase

- Ion Sequencing Pol result zero reads, no signal

LINKING METHODS, COMPOSITIONS, SYSTEMS, KITS AND APPARATUSES

BACKGROUND

The ability of enzymes to catalyze biological reactions is is fundamental to life. A range of biological applications use enzymes to synthesize various biomolecules in vitro. One particularly useful class of enzymes are the polymerases, which can catalyze the polymerization of biomolecules (e.g., nucleotides or amino acids) into biopolymers (e.g., nucleic acids or peptides). For example, polymerases that can polymerize nucleotides into nucleic acids, particularly in a template-dependent fashion, are useful in recombinant DNA technology and nucleic acid sequencing applications. Many nucleic acid sequencing methods monitor nucleotide incorporations during in vitro template-dependent replication of a target nucleic acid molecule by a polymerase.

When using an enzyme to catalyze a biological reaction of interest, it can be useful to confine the enzyme so that it is co-localized with its substrate. Such co-localization can increase the rate or efficiency of enzymatic catalysis, thereby increasing the enzymatic activity and/or product yield under a given set of reaction conditions. Various methods of co-localizing enzymes with substrates, typically by immobilizing the enzyme on a support that is then contacted with a solution including the substrate, have been reported. However, such methods typically cause a reduction in enzyme activity and succeed only at low efficiencies. Such methods typically also require modification of the enzyme prior to or after enzyme immobilization, which can be time-consuming and technically challenging to perform. There remains a need in the art for simple, efficient and reliable methods to tether enzymes to, or in the vicinity of, their target substrates so as to increase the rate or product yield of the enzymatic reaction, as well as more generally to tether proteins to desired locations.

DETAILED DESCRIPTION OF THE DRAWINGS

FIGS. 1A-1D depict exemplary embodiments of steps in constructing a tethered polymerase. FIG. 1A depicts a tether structure including a polynucleotide sequences, a primary amine at the 5' end and a FAM group at the 3' end. FIG. 1B depicts the tether structure and SMCC. FIG. 1C depicts the tether + SMCC reaction and the resulting product. FIG. 1D depicts tethers linked to two cysteine residues of Bst polymerase.

FIG. 3 depicts exemplary results of SMCC activation of FAM-labeled tether oligonucleotides and a maleimide-oligonucleotide-FAM product.

DETAILED DESCRIPTION

Figure 1A:
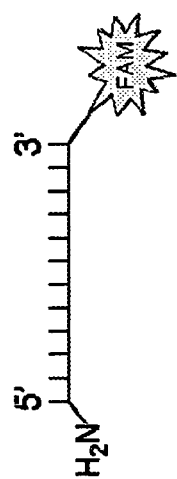

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is explicitly or implicitly set forth herein that is contrary to or otherwise inconsistent with any definition set forth in the patents, patent applications, published applications, and other publications that are herein incorporated by reference, the definition and/or description set forth herein prevails over the definition that is incorporated by reference.

The practice of the disclosure will employ, unless otherwise indicated, conventional techniques of molecular biology, microbiology and recombinant DNA techniques, which are within the skill of the art. Such techniques are explained fully in the literature. See, for example, Sambrook, J., and Russell, D. W., 2001, Molecular Cloning: A Laboratory Manual, Third Edition; Ausubel, F. M., et al., eds., 2002, Short Protocols In Molecular Biology, Fifth Edition.

As used herein, the terms "a," "an," and "the" and similar referents used herein are to be construed to cover both the singular and the plural unless their usage in context indicates otherwise. Accordingly, the use of the word "a" or "an" when used in the claims or specification, including when used in conjunction with the term "comprising", may mean "one," but it is also consistent with the meaning of "one or more," "at least one," and "one or more than one."

As used herein, the terms "link", "linked", "linkage" and variants thereof comprise any type of fusion, bond, adherence or association that is of sufficient stability to withstand use in the particular biological application of interest. Such linkage can comprise, for example, covalent, ionic, hydrogen, dipole-dipole, hydrophilic, hydrophobic, or affinity bonding, bonds or associations involving van der Waals forces, mechanical bonding, and the like. Optionally, such linkage can occur between a combination of different molecules, including but not limited to: between a nanoparticle and a protein; between a protein and a label; between a linker and a functionalized nanoparticle; between a linker and a protein; between a nucleotide and a label; and the like. Some examples of linkages can be found, for example, in Hermanson, G., Bioconjugate Techniques, Second Edition (2008); Aslam, M., Dent, A., Bioconjugation: Protein Coupling Techniques for the Biomedical Sciences, London: Macmillan (1998); Aslam, M., Dent, A., Bioconjugation: Protein Coupling Techniques for the Biomedical Sciences, London: Macmillan (1998).

In some embodiments, the disclosure relates generally to methods (as well as related compositions, systems, kits and apparatus) comprising link proteins to target compounds and/or to locations of interest using tethers. For example, the tether can be used to link the protein to a target compound, for example, to link an enzyme to a substrate. Similarly, the tether can be used to link the protein at or near a desired location on a surface. In one group of embodiments, the tether includes a polynucleotide and the target compound or location on the surface includes another polynucleotide that is capable of hybridizing to the tether. In such embodiments, the tether can be used to link the protein to the target compound or location using nucleic acid hybridization.

Linking proteins to desired targets or locations by exploiting the ability of nucleic acid molecules to selectively hybridize to each other has several advantages. For example, methods of affixing nucleic acids to surfaces, optionally in array format, are well-developed and can easily be adapted for use in protein-based assays. Similarly, the use of nucleic acid hybridization as a tethering mechanism is simple to perform, can be reversed at will via appropriate adjustment of reaction conditions, can be employed using native (i.e., unmodified) nucleic acid molecules and eliminates the need to use binding catalysts or other reactants. Furthermore, by exploiting the ability of polynucleotides to hybridize with each other in a sequence-specific manner, reactions can be performed in multiplex format where different groups of protein are selectively linked to different targets or locations using the same linking conditions.

The use of tethering mechanisms can also be useful in decreasing the cost or effort associated with perfoming protein-based applications. For example, many such applications (e.g., enzyme reactions) can consume large amounts of protein, which can be costly and time-consuming to prepare. This problem is aggravated when using proteins in methods that monitor and detect aggregate signals from a population of protein molecules acting upon a population of targets, either in asynchronous (e.g., single molecule) or synchronous format. This problem can be especially intractable when multiple rounds of washing or reagent exchange are involved. In such methods, it can be very costly to repeatedly provide proteins for each fresh round of reaction, particularly at sufficiently high concentrations to permit reaction of the protein with a target. In such situations, the use of tethers to link the protein to the target or to a surface can eliminate loss of proteins during reaction washes, thereby reducing or eliminating the need to replenish the protein in the reaction following each wash. For example, multiple reaction and wash cycles can be performed without consuming large amounts of expensive protein reagents in each wash.

Tethering can also effectively increase the local concentration of the protein within the zone of reaction with a target, thus effectively increase the rate of reaction and/or increasing the total amount of product formed within a given amount of time. For example, tethering of an enzyme can increase the rate of an enzyme-catalyzed reaction. Typically, such rate is limited by enzyme concentration; tethering limits the ability of the enzyme to diffuse away from the reaction site, effectively increasing the localized protein concentration without requiring the use of very large amounts of protein.

Finally, use of tethered proteins can sometimes increase the spectrum of reaction conditions available to the user. For example, protein tethering can permit the use of reaction conditions that enhance protein activity but would otherwise cause loss of untethered proteins from the reaction mixture. Described further herein are some exemplary embodiments that further illustrate the various advantages of tethered proteins. For example, use of a tethered polymerase in nucleotide incorporation and/or primer extension applications, such as cyclical ("step-wise") sequencing-by-synthesis reactions, can reduce the amount of polymerase consumed in each extension step, can increase the reaction rate and/or the total amount of product formed under given reaction conditions and can also permit the use of high-salt reaction conditions without significant loss of polymerase between washes, thus effectively increasing the amount of signal obtained from each extension and reducing the amount of incomplete extensions at each step.

In some embodiments, the disclosure relates generally to methods, compositions, systems, apparatuses and kits for linking a protein to a surface, comprising: contacting a tethered protein with a surface, where the tethered protein includes a tether linked to protein, and where the tether of the tethered protein includes a surface-reactive moiety and the surface includes a tether-reactive moiety that is capable of reacting with the surface-reactive moiety; and forming a linkage between the surface-reactive moiety with the tether-reactive moiety, thereby linking the tethered protein to the surface. In some embodiments, the tether reactive moiety and the surface-reactive moiety each comprise one of two complementary members of a binding pair. The binding pair can be selected from a group consisting of: a biotin moiety and an avidin moiety, an antigenic epitope and an antibody or immunogically reactive fragment thereof, an antibody and a hapten, a digoxigen moiety and an anti-digoxigen antibody, a fluorescein moiety and an anti-fluorescein antibody, an operator and a repressor, a nuclease and a nucleotide, a lectin and a polysaccharide, a steroid and a steroid-binding protein, an active compound and an active compound receptor, a hormone and a hormone receptor, an enzyme and a substrate, an immunoglobulin and protein A, and two polynucleotides that are complementary to each other over at least some portion of their respective lengths (where complementarity is optionally defined according to conventional Watson-Crick base pairing rules or alternatively according to some other base-pairing paradigm).

In some embodiments, the surface-reactive moiety of the tether includes a first polynucleotide having a first polynucleotide sequence, and the tether-reactive moiety of the surface includes a second polynucleotide having a second polynucleotide sequence, where the first and second polynucleotide sequences are at least 80% complementary to each other (where complementarity is optionally defined according to conventional Watson-Crick base pairing rules or alternatively according to some other base-pairing paradigm). In some embodiments, the first and second polynucleotide sequences are at least 85%, at least 90%, at least 95%, at least 97% or at least 99% complementary to each other.

In some embodiments, the disclosure relates generally to methods (and related compositions, systems, apparatuses and kits) for linking a protein to a surface, comprising: binding a tethered protein to a surface, where the tethered protein includes a protein linked to a tether, the tether including a first polynucleotide and the first polynucleotide including a first polynucleotide sequence; where the binding further includes contacting the tethered protein with a second polynucleotide, wherein the second polynucleotide is linked to a surface and includes a second polynucleotide sequence that is at least 80% complementary to the first polynucleotide sequence, and hybridizing the first polynucleotide sequence to the second polynucleotide sequence, thereby linking the tethered polymerase to the surface. In some embodiments, the first and second polynucleotide sequences are at least 80% complementary to each other (where complementarity is optionally defined according to conventional Watson-Crick base pairing rules or alternatively according to some other base-pairing paradigm). In some embodiments, the first and second polynucleotide sequences are at least 85%, at least 90%, at least 95%, at least 97% or at least 99% complementary to each other.

In some embodiments, the disclosure relates generally to methods, compositions, systems, apparatuses and kits useful for co-localizing an enzyme and its substrate using a tether to link the enzyme to, or in the vicinity of, the substrate. In some embodiments, the colocalization can be performed prior to, or during, the reaction of the enzyme with the substrate. Such co-localization can increase the rate of the enzymatic reaction and/or increase the the product yield.

In some embodiments, the disclosure relates generally to methods of co-localizing an enzyme with a substrate by linking an enzyme (or any biologically active fragment thereof) to a substrate using a tether, thereby forming an tethered enzyme-substrate complex that includes the enzyme (or biologically active fragment) linked to the substrate through the tether. Typically, the linking is done in such a manner that the enzyme (or biologically active fragment) retains enzymatic activity and can still react with the substrate to form a product after the linking is complete. In one exemplary embodiment, the enzyme-reactive moiety of the tether can be linked to the enzyme (or biologically active fragment) to form a tethered enzyme. The tethered enzyme can be contacted with the substrate under conditions where the substrate-reactive moiety of the tether in the tethered enzyme binds to the substrate, thereby forming a tethered enzyme-substrate complex that includes the enzyme linked to the substrate through the tether. Optionally, the tethered enzyme-substrate complex retains enzymatic activity. For example, the enzyme (or biologically active fragment) of the tethered enzyme-substrate complex can bind to the substrate within the tethered enzyme-substrate complex, or to any other substrate molecule within the reaction mixture, and can catalyze the enzyme-substrate reaction. In some embodiments, the substrate is linked to a surface, such that formation of the tethered enzyme-substrate complex effectively localizes the enzyme (or biologically active fragment) to the surface.

In some embodiments, the tether is not used to link the enzyme to the substrate, but is instead used to link the enzyme to a surface. For example, the tether can link the enzyme to to the surface, thereby forming a surface-linked tethered enzyme, while the substrate can be free-floating or independently attached to the same or different surface. In some embodiments, the substrate is linked to the same surface as the the tethered enzyme. For example, the enzyme and substrate can each be independently linked to the same surface at attachment sites that are sufficiently close to each other, and where the tether is sufficiently flexible, to permit reaction of the enzyme with the substrate.

In some embodiments, the disclosure relates generally to methods (and related compositions, systems, kits and apparatuses) for co-localizing an enzyme and its substrate comprising: forming a tethered enzyme by linking a tether to the enzyme (or biologically active fragment thereof), where the tethered enzyme retains enzymatic activity; and binding the tethered enzyme to a substrate. Optionally, the tether includes an enzyme-reactive moiety, and the linking further includes reacting the enzyme-reactive moiety with the enzyme, thereby forming an enzyme-tether linkage that links the tether to the enzyme. The linkage can be a covalent linkage, an electrostatic linkage or any other linkage suitable for linking the enzyme (or biologically active fragment) to the tether. In some embodiments, the tether includes a substrate-reactive moiety, and the disclosed methods (and related compositions, systems, kits and apparatuses) further involve linking the tether to the substrate by reacting the substrate-reactive moiety with the substrate, and the linking further includes reacting the substrate-reactive moiety with the substrate, thereby forming an substrate-tether linkage that links the tether to the substrate. In some embodiments, the enzyme in the tethered enzyme selected from the group consisting of: a polymerase, a ribosome, a helicase, a pyrophosphatase and an apyrase.

In some embodiments, the disclosure relates generally to methods (and related compositions, systems, apparatuses and kits) for linking polymerases to target compounds, or to desired locations of interest. In some embodiments, the polymerase can include that is capable of catalyzing the incorporation of one or more nucleotides into a nucleic acid molecule. Typically but not necessarily such nucleotide incorporation can occur in a template-dependent fashion. The polymerase can be a naturally-occurring polymerase, or any subunit or truncation thereof, a mutant, variant, derivative, recombinant, fusion, modified, chemically modified, or otherwise engineered form of any polymerase, a synthetic molecule or assembly that can catalyze nucleotide incorporation, as well as analogs, derivatives or fragments thereof that retain the ability to catalyze such nucleotide incorporation. Optionally, the polymerase can be a mutant polymerase comprising one or more mutations involving the replacement of one or more amino acids with other amino acids, the insertion or deletion of one or more amino acids, or the linkage of parts of two or more polymerases. Typically, the polymerase comprises one or more active sites at which nucleotide binding and/or catalysis of nucleotide polymerization can occur. Some exemplary polymerases include without limitation DNA polymerases including both DNA-dependent and RNA-dependent DNA polymerases (such as for example Bst DNA polymerase, Therminator™ polymerase, KOD polymerase, Phi-29 DNA polymerase, reverse transcriptases and *E. coli* DNA polymerase) and RNA polymerases. In some embodiments, the polymerase is a fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. In one exemplary embodiment, the polymerase is Phusion® DNA polymerase (New England Biolabs), which comprises a *Pyrococcus*-like polymerase fused to a processivity-enhancing domain as described, for example, in U.S. Pat. No. 6,627,424.

Typically, the polymerase includes a nucleic acid binding site and a polymerase active site. The polymerase active site can be a site of polymerase activity. The polymerase activity can comprise any in vivo or in vitro enzymatic activity of the polymerase that relates to catalyzing the incorporation of one or more nucleotides into a nucleic acid molecule, for example, primer extension activity and the like. Typically, but not necessarily such nucleotide polymerization occurs in a template-dependent fashion. In addition to such polymerase activity, the polymerase can possess other activities such as DNA binding activity, 3' to 5' or 5' to 3' exonuclease activity, and the like.

In some embodiments, the disclosure relates generally to methods (and related compositions, systems, kits and apparatuses) for linking a polymerase to a surface, comprising: contacting a tethered polymerase with a surface, where the tethered polymerase includes polymerase linked to a tether including a first polynucleotide, where the polynucleotide has a first polynucleotide sequence, and the surface includes a second polynucleotide including a second polynucleotide sequence, where the first and second polynucleotide sequences are at least 80% complementary to each other;

and hybridizing the first polynucleotide sequence to the second polynucleotide sequence, thereby linking the tethered polymerase to the surface.

In some embodiments, the first polynucleotide of the tether is covalently linked to an amino acid residue of the polymerase. For example, the first polynucleotide can be covalently linked to a cysteine residue of the polymerase. The first polynucleotide can be covalently linked to the cysteine residue through a flexible linker.

Typically, the tethered polymerase has polymerase activity, and can catalyze the incorporation of one or more nucleotides into a nucleic acid molecule.

In some embodiments, the disclosed methods (and related compositions, systems, kits and apparatuses) can further include contacting the tethered polymerase with one or more nucleotides.

In some embodiments, the disclosed methods (and related compositions, systems, kits and apparatuses) can further include incorporating one or more nucleotides into the second polynucleotide using the tethered polymerase. For example, the tethered polymerase can polymerize the one or more nucleotides onto the 3' end of the second polynucleotide.

In some embodiments, the surface includes a third polynucleotide, and the disclosed methods (and related compositions, systems, kits and apparatuses) can further include incorporating one or more nucleotides into the third polynucleotide using the tethered polymerase. For example, the tethered polymerase can polymerize the one or more nucleotides onto the 3' end of the third polynucleotide.

In some embodiments, the disclosure relates generally to compositions (as well as related methods, systems, kits and apparatus) comprising tethered proteins, where the tether can be fixed to a site of interest. For example, the tether can link the protein to a substrate or to a surface.

In some embodiments, the disclosure relates generally to compositions (and related methods, systems, kits and apparatuses) comprising tethered enzymes. Typically, the tethered enzyme includes an enzyme linked to a tether, where the tethered enzyme has enzymatic activity.

In some embodiments, the tether is a linear tether. In some embodiments, the tether can include a linear polymer, which can be rigid or flexible. In some embodiments, the tether includes a polynucleotide. In some embodiments, the tether includes a flexible linker. In some embodiments, the flexible linker can have a persistence length of up to about 200 nm; for example between about 0.5 nm and about 1500 nm; typically between about 1.0 nm and about 15 nm or between about 1.5 nm and about 10 nm; even more typically between about 1.5 nm and 5.0 nm, where the persistence length is measured under any reaction conditions that are suitable for primer extension (for example, in a buffer comprising between 0 and about 2M salt (e.g., NaCl or $MgCl_2$)), even more typically in a buffer comprising between 0 and about 100 mM salt (e.g., NaCl or $MgCl_2$). Methods of measuring persistence length of polynucleotides in solution are known in the art; see, e.g., Murphy et al., "Probing Single Stranded DNA Conformational Flexibility Using Fluorescence Spectroscopy", Biophys J. 2004 April; 86(4): 2530-2537. In some embodiments, the flexible linker includes a polynucleotide. In some embodiments, the flexible linker includes a polypeptide. In some embodiments, the flexible linker includes polyethylene glycol.

Optionally, the tether can include one or more labels. The one or more labels can be detected using any suitable detection system. For example the one or more labels can include fluorescent labels, luminescent labels, chemically detectable labels, or magnetically detectable labels.

In some embodiments, the tether can include one or more reactive moieties. In some embodiments, the tether includes an enzyme-reactive moiety. The enzyme-reactive moiety can react with the enzyme under suitable conditions. Reaction of the enzyme-reactive moiety with the enzyme can result in the formation of an enzyme-tether linkage that links the tether to the enzyme, thereby forming a tethered enzyme. The enzyme-tether linkage can include one or more bonds selected from the group consisting of: a covalent bond, an electrostatic bond, an affinity-based interaction and a hydrogen bond. In some embodiments, the enzyme-reactive moiety of the tether reacts with a sulfhydryl group of a cysteine residue of the enzyme and forms a covalent bond with a sulfur atom of the sulfhydryl group of the cysteine. In some embodiments, the enzyme-reactive moiety of the tether reacts with an amino group of an amino acid residue of the enzyme. The amino group can be located on an N-terminal amino acid residue of the enzyme. In some embodiments, the enzyme-reactive moiety of the tether reacts with a carboxyl group of an amino acid residue of the enzyme. The carboxyl group can be located on a C-terminal amino acid residue of the enzyme.

In some embodiments, the enzyme includes a reactive sulfhydryl group (for example, a sulfhydryl group of a cysteine residue, that is optionally a surface cysteine) and the enzyme-reactive moiety of the tether includes a linking group that is capable of reacting with the sulfhydryl group of the cysteine reside. For example, the linking group can include a reactive amine that can be activated by suitable treatment (e.g., reaction with SMCC) to form a reactive maleimide. The tether including the reactive maleimide can then be contacted with the enzyme under suitable conditions where the reactive maleimide group reacts with the sulfhydryl group of the cysteine, forming a covalent linkage, typically a linkage comprising a thioether bond.

In some embodiments, the tether includes a substrate-reactive moiety. The substrate-reactive moiety can react with the substrate under suitable conditions. For example, the substrate-reactive moiety can react or bind selectively to the substrate when contacted with the substrate Reaction of the substrate-reactive moiety with the substrate can result in the formation of a substrate-tether linkage that links the tether to the substrate. The substrate-tether linkage can include one or more bonds selected from the group consisting of: a covalent bond, an electrostatic bond, an affinity-based interaction and a hydrogen bond. In one exemplary embodiment, the substrate-reactive moiety of the tether comprises a first polynucleotide including a first polynucleotide sequence, and the substrate includes, e.g., is linked to, a second polynucleotide including a second polynucleotide sequence, where the first and second polynucleotide sequences are at least 80% complementary to each other. When the tether and substrate are contacted with each other under hybridization conditions, then first and second polynucleotide sequences hybridize to each other, thereby forming a nucleic acid duplex that links the tether to the substrate.

In some embodiments, the tether of the tethered enzyme includes a surface-reactive moiety. The surface-reactive moiety can react with a surface under suitable conditions. Reaction of the surface-reactive moiety with the surface can result in the formation of a surface-tether linkage that links the tether to the surface. The surface-tether linkage can include one or more bonds selected from the group consisting of: a covalent bond, an electrostatic bond, an affinity-based interaction and a hydrogen bond.

In some embodiments, the surface-reactive moiety of the tethered enzyme includes a first polynucleotide, and the surface includes a second polynucleotide. The first and second polynucleotides may be capable of hybridizing to each other over at least a portion of their respective lengths. In some embodiments, the first polynucleotide includes a first polynucleotide sequence and the second polynucleotide includes a second polynucleotide sequence, where the first and second polynucleotide sequences are at least 80% complementary to each other. In some embodiments, the first and second polynucleotide sequences are at least 80% complementary, at least 90% complementary, at least 95% complementary, at least 97% complementary, or at least 99% complementary to each other. Typically, complementarity can be defined according to conventional Watson-Crick base pairing rules (e.g., A base pairs with T and C base pairs with G); alternatively complementarity can be defined according to non-Watson Crick base pairing paradigms as well. In some embodiments, the first polynucleotide sequence and the second polynucleotide sequence are hybridized to each other.

In some embodiments, the tether is linked to any one or more members of the group consisting of: enzyme, substrate and surface. For example, the tether can first be linked to the enzyme through the enzyme-reactive moiety of the tether, thereby forming a tethered enzyme, and the tether of the tethered enzyme can then be linked to a substrate using the substrate-reactive moiety of the tether, or alternatively linked directly to a surface using a surface-reactive moiety of the tether. Alternatively, the tether can first be linked to a substrate, or to a surface, and then be linked to the enzyme.

In a typical embodiment, the enzyme comprises a polymerase.

In some embodiments, the disclosure relates generally to a composition comprising a tethered polymerase including a polymerase linked to a tether, where the tethered polymerase has polymerase activity. The polymerase-tether linkage can include one or more bonds selected from the group consisting of: a covalent bond, an electrostatic bond, an affinity-based interaction and a hydrogen bond. In some embodiments, the polymerase can be covalently linked to the tether. The tether can be linked to an amino acid residue of the polymerase. In some embodiments, the tether is linked to a sulfhydryl group of a cysteine residue of the polymerase. In some embodiments, the tether is linked to an amino group of an amino acid residue of the polymerase. In some embodiments, the tether is linked to a carboxyl group of an amino acid residue of the polymerase. The tether can include a polynucleotide. The polymerase can be covalently linked to the polynucleotide. The polynucleotide can be covalently linked to a cysteine residue of the polymerase. In some embodiments, a 5' end of the polynucleotide is covalently linked to an amino acid residue of the polymerase. The covalent linkage between the tether and the polymerase can include a series of atoms, each atom in the series being linked covalently to the next atom in the series such that the tether and the polymerase are ultimately linked to each other through a series of atoms linked through covalent bonds.

In some embodiments, the polymerase of the tethered polymerase is linked to a first member of a binding pair, the tether is linked to a second member of the binding pair, and where the first member and the second member are linked to each other to form the tethered polymerase. The binding pair can be selected from a group consisting of: a biotin moiety and an avidin moiety, an antigenic epitope and an antibody or immunogically reactive fragment thereof, an antibody and a hapten, a digoxigen moiety and an anti-digoxigen antibody, a fluorescein moiety and an anti-fluorescein antibody, an operator and a repressor, a nuclease and a nucleotide, a lectin and a polysaccharide, a steroid and a steroid-binding protein, an active compound and an active compound receptor, a hormone and a hormone receptor, an enzyme and a substrate, an immunoglobulin and protein A, and two polynucleotides that are complementary to each other over at least some portion of their respective lengths (where complementarity can optionally be defined according to conventional Watson-Crick base pairing rules or alternatively according to some other base-pairing paradigm).

As used herein, the term "nucleotide" and its variants comprises any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally-occurring nucleotides but also any analogs, regardless of their structure, that can bind selectively to, or can be polymerized by, a polymerase. While naturally-occurring nucleotides typically comprise base, sugar and phosphate moieties, the nucleotides of the disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. Some examples of nucleotide analogs are described in Xu, U.S. Pat. No. 7,405,281. In some embodiments, the nucleotide comprises a label (e.g., reporter moiety) and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group or substitute phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

As used herein, the term "nucleotide incorporation" and its variants comprise polymerization of one or more nucleotides to form a nucleic acid strand including at least two nucleotides linked to each other, typically but not necessarily via phosphodiester bonds, although alternative linkages may be possible in the context of particular nucleotide analogs.

The following non-limiting examples are provided purely by way of illustration of exemplary embodiments, and in no way limit the scope and spirit of the present disclosure. Furthermore, it is to be understood that any inventions disclosed or claimed herein encompass all variations, combinations, and permutations of any one or more features described herein. Any one or more features may be explicitly excluded from the claims even if the specific exclusion is not set forth explicitly herein. It should also be understood that disclosure of a reagent for use in a method is intended to be synonymous with (and provide support for) that method involving the use of that reagent, according either to the specific methods disclosed herein, or other methods known in the art unless one of ordinary skill in the art would understand otherwise. In addition, where the specification and/or claims disclose a method, any one or more of the reagents disclosed herein may be used in the method, unless one of ordinary skill in the art would understand otherwise.

EXAMPLES

Example 1: Construction of a Tethered Polymerase

A tethered polymerase was constructed by covalently linking a tether including a first polynucleotide sequence to a cysteine residue of a variant Bst polymerase ("Ion Sequencing Polymerase") having the following amino acid sequence:

MAKMAFTLADRVTEEMLADKAALVVEVVEENYHDAPIVGIAVVNERGRFFL

RPETALADPQFVAWLGDETKKKSMFDSKRAAVALKWKGIELCGVSFDLLLA

AYLLDPAQGVDDVAAAAKMKQYEAVRPDEAVYGKGAKRAVPDEPVLAEHLV

RKAAAIWELERPFLDELRRNEQDRLLVELEQPLSSILAEMEFAGVKVDTKR

LEQMGKELAEQLGTVEQRIYELAGQEFNINSPKQLGVILFEKLQLPVLKKT

KTGYSTSADVLEKLAPYHEIVENILHYRQLGKLQSTYIEGLLKVVRPDTKK

VHTIFNQALTQTGRLSSTEPNLQNIPIRLEEGRKIRQAFVPSESDWLIFAA

DYSQIELRVLAHIAEDDNLMEAFRRDLDIHTKTAMDIFQVSEDEVTPNMRR

QAKAVNFGIVYGISDYGLAQNLNISRKEAAEFIERYFQSFPGVKRYMENIV

QEAKQKGYVTTLLHRRRYLPDITSRNFNVRSFAERMAMNTPIQGSAADIIK

KAMIDLNARLKEERLQAHLLLQVHDELILEAPKEEMERLCRLVPEVMEQAV

TLRVPLKVDYRYGSTWYDAK

The tether included a polynucleotide sequence complementary to the sequence of a sequencing primer P1 (described further below) and a flexible linker including a poly-A stretch, as well as a primary amine at the 5' end of tether. The 3' end of the tether was blocked using a FAM group. The structure of the tether is depicted in FIG. 1A.

Figure 1B:
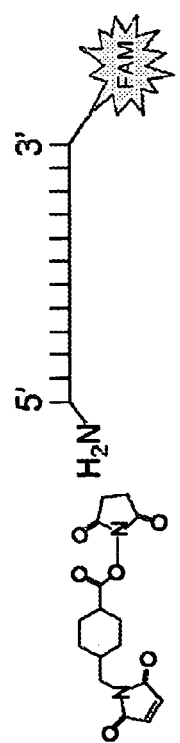
Figure 1C:
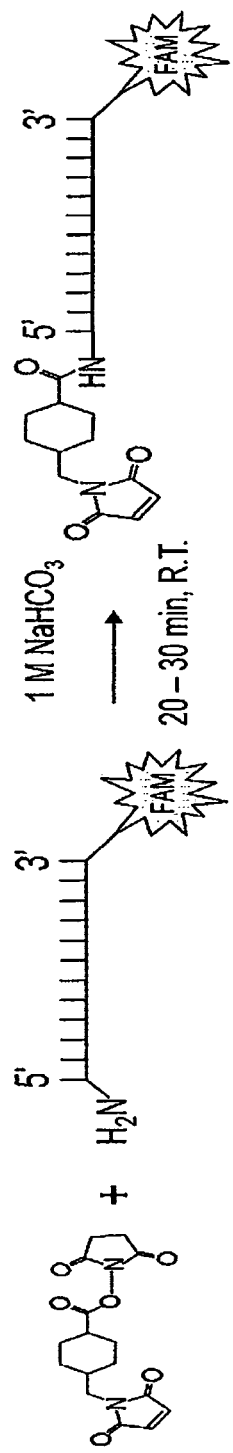

The primary amine of the tether can be activated via conversion to a maleimide group using SMCC, as shown in FIG. 1B. The reaction and resulting product is depicted in FIG. 1C.

Figure 1D:
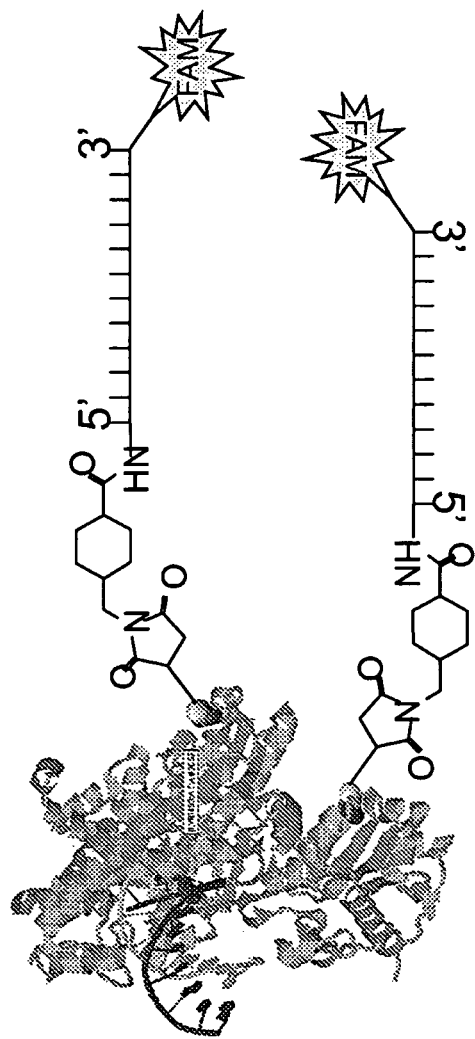

The tether of FIG. 1 was then covalently linked to two cysteine residues of the Bst Polymerase to obtain the tethered polymerase depicted in FIG. 1D according to the methods described below.

Activation of the Tether

The following reagents were used:

The tether including a 49 base-pair oligonucleotide with a tB30 amino tether and FAM; MW=16115.9; 105.7 nm=1.7 mg (IDT DNA). The structure and primary amino acid sequence of the tether can be depicted as follows:

5AmMC12/AA AAA AAA AAA AAA AAA AAA GAC TGC

CAA GGC ACA CAG GGG ATA GGA AA/36-FAM

Bst; Ion Torrent lot 7 sequencing polymerase, ~1 mg/mL

Klenow (KF) exo-wt (106.9 µM; 7.6 mg/mL; Starlight source)

AlexaFluor 647 maleimide (1 mg; A20347; MW~1300)

AlexaFluor 647 cadaverine (1 mg; A30679; MW~1000)

SMCC (Molecular Probes; 51534; Lot: 38985A; MW=334.33)

sulfo-SMCC (Molecular Biosciences; MW=463.37)

sodium bicarbonate (J.T. BAKER; 3506-1; FW 84.01)

Figure 2:
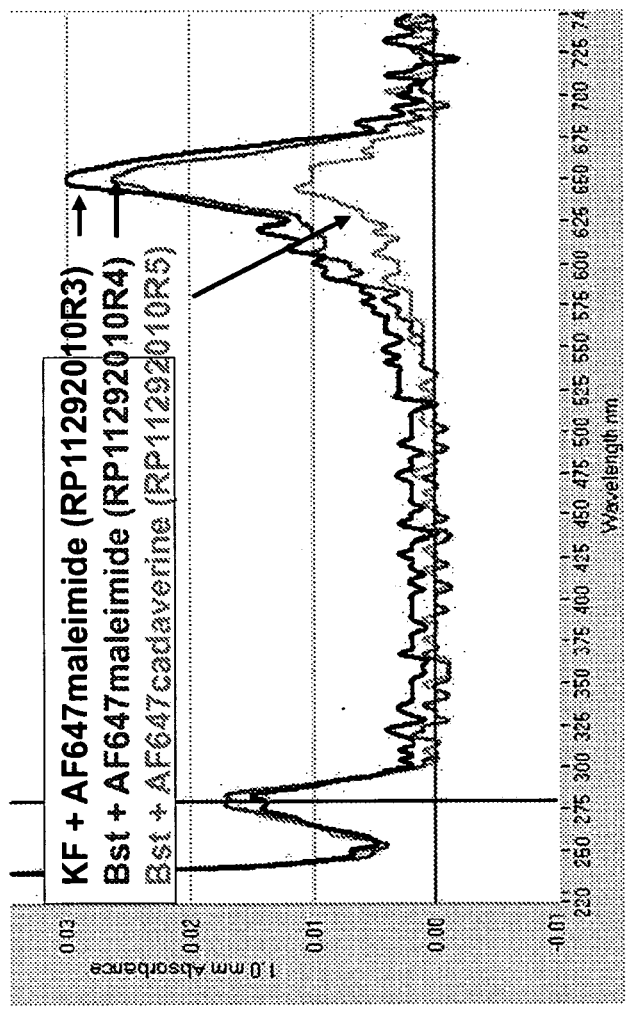
FIG. 2 depicts exemplary results of labeling polymerases with AF647 maleimide.

The Bst polymerase was then labeled with maleimide dye (AF647 maleimide). Results are depicted in FIG. 2.

The tether including the FAM-labeled oligonucleotide was activated with SMCC to generate a maleimide-oligo-FAM product. Representative results of the activation reaction are depicted in FIG. 3.

The maleimide-oligo-FAM product was purified with NAP-5 column

Figure 4:
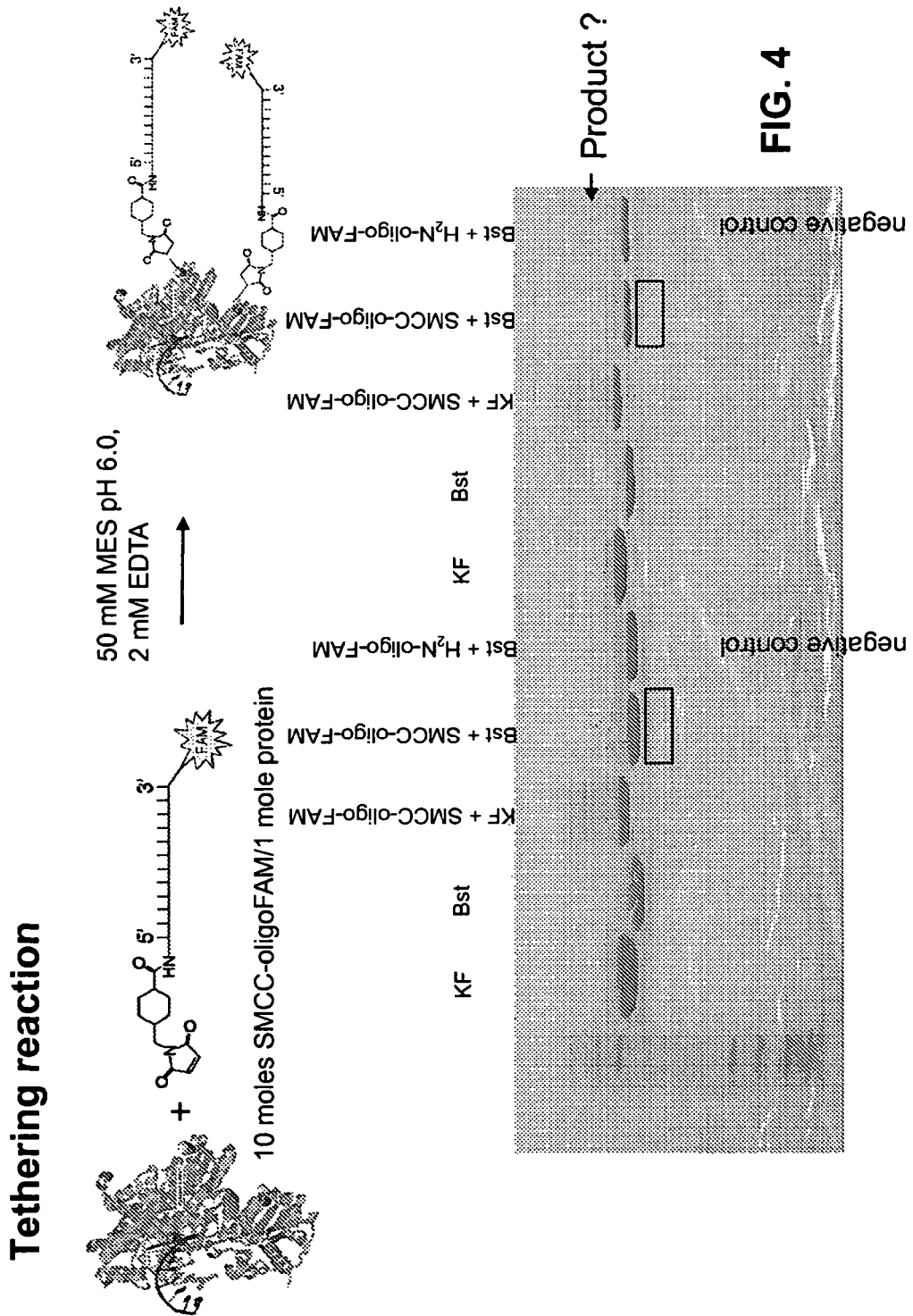
FIG. 4 depicts a tethering reaction and gel analysis of exemplary reaction products with Klenow fragment (KF) and Bst polymerases.

Two different polymerases, Klenow fragment ("KF") and the variant Bst polymerase ("Bst") were reacted with maleimide-oligo-FAM to form tethered polymerases, and the reaction products were purified on a gel. Representative results are depicted in FIG. 4. A possible product band was detected using gel analysis using less than 10% of the reaction.

Linkage of the Polymerase to the Tether

The following protocol was used to link the polymerase to the tether:

(a) Polymerase DTT Treatment and Purification to Reduce Disulfide Bonds:

Reagents (Stock Concentration) and Materials:

Lot 7 sequencing Bst polymerase (~1 mg/mL), DTT (1 M),

Tris pH 8.5 (1 M), Exchange Buffer (50 mM Mes pH 6.0, 2 mM EDTA) NAP-5 column (G.E. NAP column, product#17-0853-02), Amicon 30K centrifugal filter (Millipore Cat No. UFC503096 Lot No. ROMA72710), 1-1.5 mL Eppendorf Tubes Protocol:

Mix Bst polymerase (25 µL), DTT (1 µL), Tris pH 8.5 (5 µL) and ddH$_2$O (69 µL). Incubate at 4° C. for 1-12 h. Purify Bst polymerase using a NAP-5 column Use gravity flow to prepare and use the NAP-5 column: (1) drain storage buffer (2) add exchange buffer and pass >15 mL exchange buffer (3) add reaction mix and drain until all of the mix has entered the matrix and (4) fill column with exchange buffer and (6) collect 5 drop fractions. Next use the Nanodrop to determine in which fraction(s) contain the Bst polymerase. Pool the fractions and concentrate using the Amicon 30K centrifugal filter using the manufacture's instructions.

(Amicon Protocol: spin for 7 min at 11,000×g. Transfer filter to clean collection tube and insert in an inverted manner. Spin for 1 mM at 1000×g). Measure the absorbance of the concentated Bst polymerase using the Nanodrop and determine the Bst concentration using the following formula:

$\epsilon_{280}=58000/Mcm.$

Figure 5:
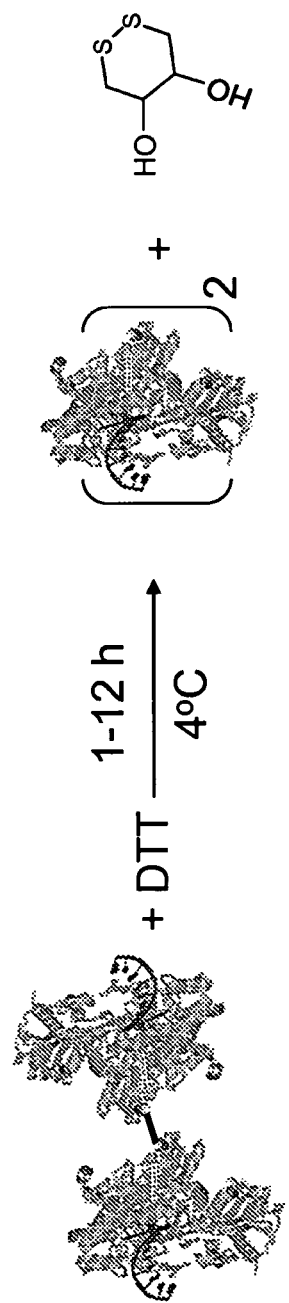
FIG. 5 depicts an embodiment of a reaction using DTT to reduce disulfide bonds of the polymerase.

The reaction is depicted in FIG. 5.

(b) Activation of FAM-Oligo with SMCC

The oligo tether was activated using SMCC to generate a FAM-oligo derivatized with maleimide Reagents:
SMCC (MW=334.33 g/mol; Molecular Probes; product #:S1534; Lot:38985A),
Sodium bicarbonate (J.T. Baker; product #:3506-01)
FAM-oligo (tB30 Amino tether FAM; MW=16115.9; 105.7 nm=1.7 mg),
DMSO Protocol:
FAM-oligo was dissolved in ddH$_2$O to obtain a 500 µM concentration. Approximately 1 mg of SMCC was weighed and dissolved with DMSO to prepare a 20 mM concentration. The following reaction mix was prepared: FAM-oligo (20 µL), NaHCO3 (20 µL) and SMCC (10 µL). The reaction was incubated at room temperature for 20-30 mM The product was purified using a NAP-5 column. The same protocol to purify the polymerase was used to purify the product. The fractions were identified with UV-Vis (nanodrop). An aliquot of the identified fraction was diluted with an equal amount of 250 mM phosphate (pH 9) to measure the absorbance of FAM and use a molar extinction coefficient of $\epsilon_{510}=58000/Mcm$ to determine the FAM concentration. Analytical HPLC confirmed that the desired product. However, an additional peak was also observed. This corresponding peak is probably the product with a hydrolyzed maleimide. Reducing the reaction pH and time minimizes the production of this product.

Figure 6:
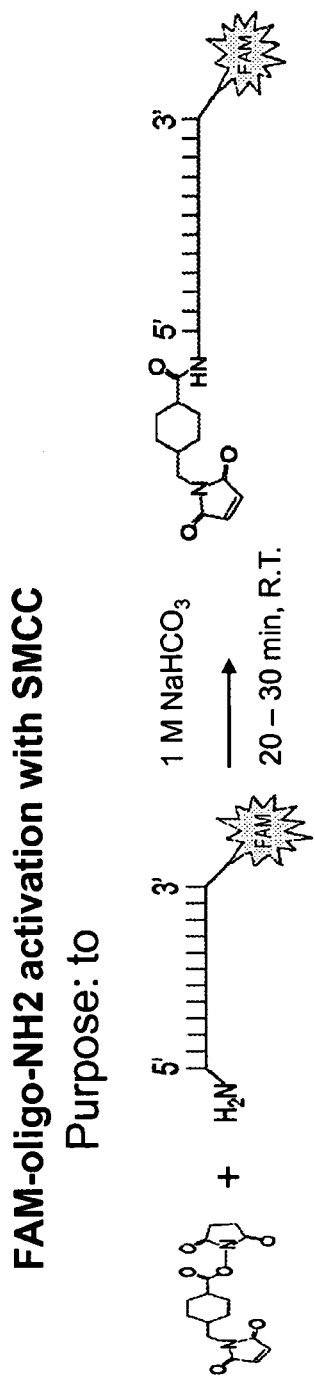
FIG. 6 depicts an embodiment of an activation reaction of FAM-oligonucleotide + SMCC to form a derivatized FAM-oligonucleotide product.

The reaction is depicted in FIG. 6.

(c) Linking the Tether to the Polymerase

Figure 7:
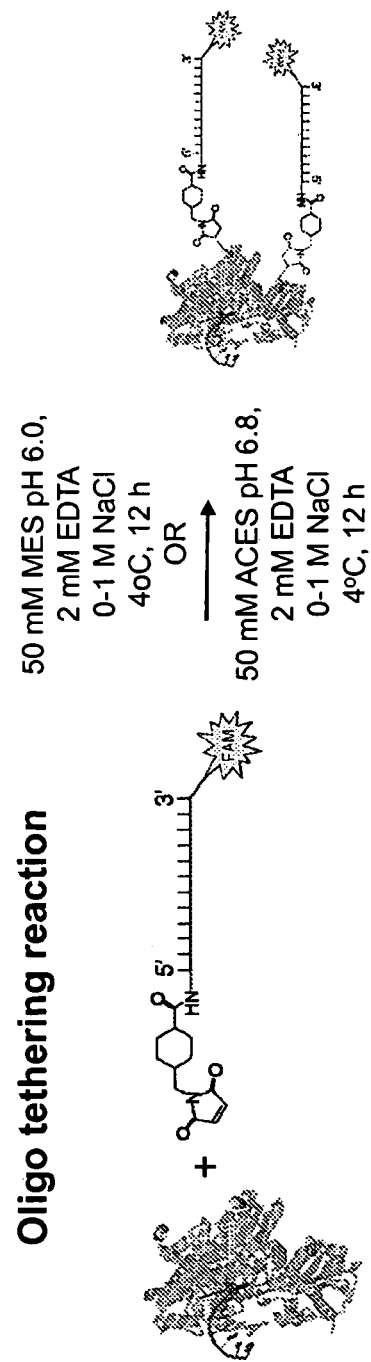
FIG. 7 depicts an embodiment of a tethering reaction of a polymerase + derivatized FAM-oligonucleotide tether to form a polymerase linked to oligonucleotide tethers.

The tether was linked to the polymerase to form a tethered polymerase as follows:

Reagents:
Bst (DTT treated and purified),
FAM-oligo-Maleimide (freshly prepared)
Exchange buffer (50 mM MES pH 6.0, 2 mM EDTA or 50 mM ACES pH 6.8, 2 mM EDTA)
NaCl Protocol:
Mix Bst and FAM-oligo-maleimide in exchange buffer in the presence of 0.5-1 M NaCl.
Incubate reaction at 4° C. for ~12 h The reaction is depicted in FIG. 7.

Figure 8:
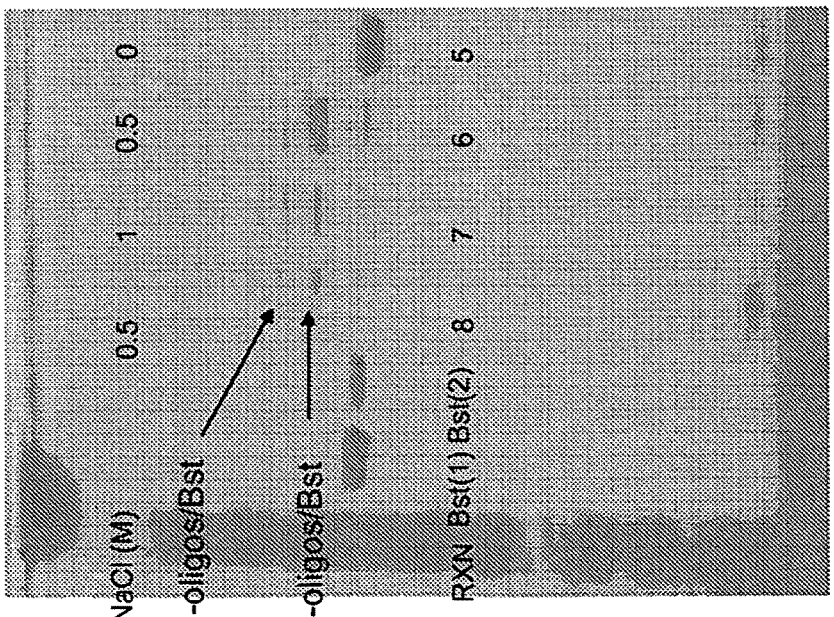
FIG. 8 depicts exemplary results of oligonucleotide tethering reactions performed with varying salt concentrations.

As depicted in FIG. 8, the use of varying salt concentrations in the exchange buffer resulted in different product yields, with the inclusion of NaCl pushing the reaction yield to greater than 50%.

Example 2: Use of Tethered Polymerase for Nucleic Acid Sequencing

The tethered polymerase of the prior Example, comprising a Bst polymerase linked to an oligonucleotide tether, was used in an ion-based sequencing reaction using the Ion Torrent PGM sequencing platform (Life Technologies).

Figure 9:
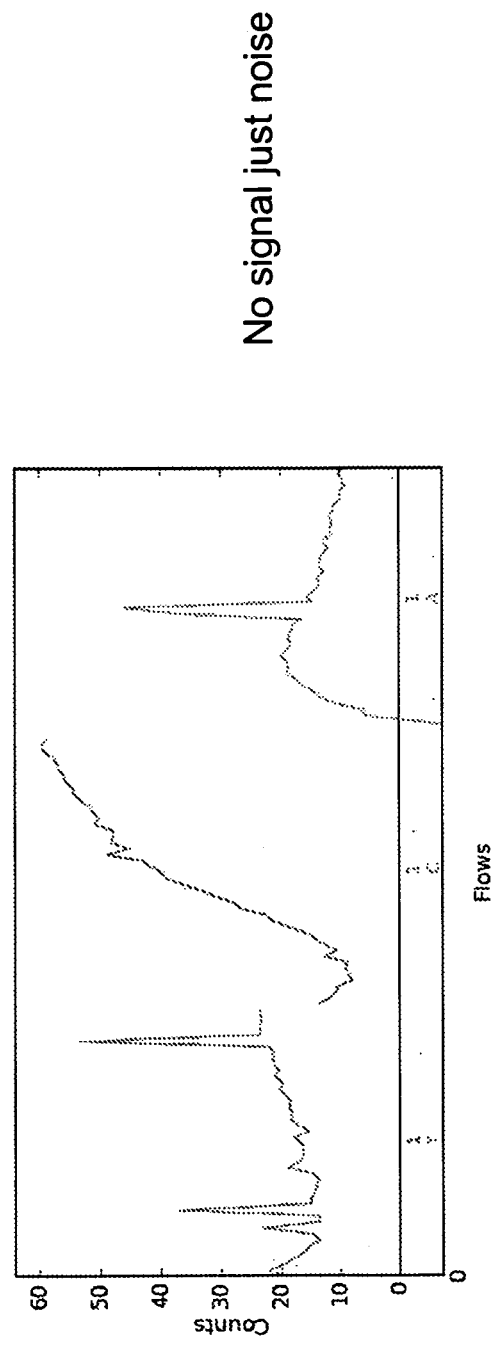
FIG. 9 depicts exemplary results of sequencing reactions using an untethered sequencing polymerase.
Figure 10:
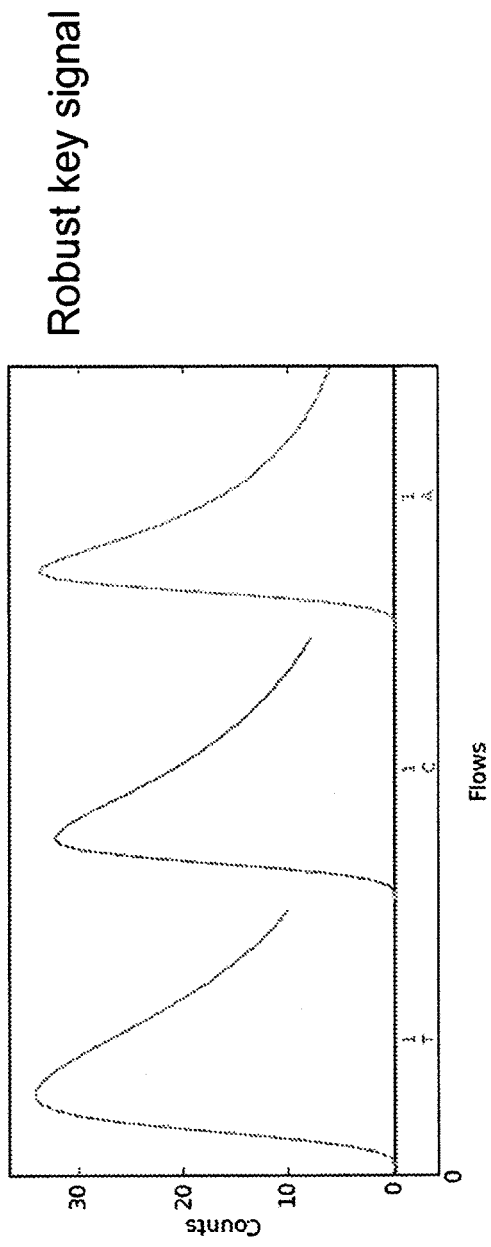
FIG. 10 depicts exemplary results of sequencing reactions using a sequencing polymerase tethered with an oligonucleotide.

Both tethered polymerase and corresponding untethered polymerase (control) were bound to to ssDNA beads and washed with high salt. The sequencing primer was then hybridized to the ssDNA template. Following hybridization, the beads were run in a standard sequencing reaction on the Ion Torrent PGM Sequencing platform. As depicted in FIG. 9 and FIG. 10 sequencing using high-salt washes between successive extensions in the PGM platform was observed to be supported by the tethered polymerase of Example 1, but not with the corresponding (control) untethered polymerase. The use of high salt buffers is advantageous because it increases polymerase activity.

As depicted in FIG. 9, the Ion Sequencing Polymerase (in untethered form) was observed to bind Ion Spheres (beads) with ssDNA template in the Ion W2 reagent (6.3 mM MgCl$_2$, 13 mM NaCl, 0.01% TritonX-100, pH 7.5) with low affinity and could be washed off with increasing ionic strength. At 1 M NaCl, 100% of Ion Sequencing Polymerase 1.0 was washed off Ion Spheres.

As depicted in FIG. 10, the Ion Sequencing Polymerase tethered with an oligo as described in Example 1, where the tether immobilizes the tethered polymerase to the ssDNA template, was observed to remain on the Ion beads under high salt conditions as the tethered polymerase was not washed off in these conditions. High salt is not expected to harm the polymerase except to wash it from the ssDNA.

The performance of the Ion Sequencing Polymerase in both tethered and untethered (control) forms in an Ion PGM Sequencing system was measured and compared.

The untethered form of the Ion Sequencing Polymerase exhibited no signal using high salt sequencing conditions (20 mM MgCl2, 200 mM NaCl, 0.01% Triton X-100, pH 7.5), and no observable sequencing reads were obtained.

In contrast, the tethered Ion Sequencing Polymerase demonstrated robust sequencing performance using the high salt sequencing conditions (20 mM MgCl2, 200 mM NaCl, 0.01% Triton X-100, pH 7.5), where over 800,000 Q17 reads were obtained and over 30 key signals detected from a single sequencing reaction. As these results indicate, PGM sequencing at high salt (>200 mM ionic strength) is supported by the tethered Ion Sequencing Polymerase but not by the untethered Ion Sequencing Polymerase.

What is claimed:

1. A composition comprising an active B st DNA polymerase enzyme, or a mutant or fragment thereof that can catalyze nucleotide incorporation, covalently linked to a first polynucleotide, a second polynucleotide which is hybridized to the first polynucleotide and a sequencing primer capable of hybridizing to the second polynucleotide, wherein the second polynucleotide is a single stranded DNA (ssDNA) template that is covalently linked to a surface and wherein the composition is present in an aqueous solution with an ionic strength equal to or greater than 200 mM.

2. The composition of claim 1, wherein the first polynucleotide is covalently linked to an amino acid residue of the active Bst DNA polymerase enzyme.

3. The composition of claim 1, wherein the first polynucleotide is covalently linked to a cysteine residue of the active Bst DNA polymerase enzyme.

4. The composition of claim 1, further comprising one or more nucleotides.

5. The composition of claim 1, wherein the surface further comprises a third polynucleotide.

6. A composition comprising: an active Bst DNA polymerase enzyme, or a mutant or fragment thereof that can catalyze nucleotide incorporation, having an amino acid residue that is covalently linked to one end of a first polynucleotide, wherein the first polynucleotide is hybridized to a second polynucleotide, wherein the second polynucleotide is a single stranded DNA (ssDNA) template with one end covalently linked to a surface and wherein the composition is present in an aqueous solution of a sequencing by synthesis reaction mixture with an ionic strength equal to or greater than 200 mM.

7. The composition of claim 6, wherein the amino acid residue comprises a cysteine residue of the polymerase.

8. The composition of claim 6, further comprising one or more nucleotides.

9. The composition of claim 1, wherein the second polynucleotide is covalently attached to the surface of a bead.

10. The composition of claim 1, comprising a population of identical ssDNA templates covalently linked to the surface.

11. The composition of claim 1, wherein the Bst DNA polymerase is a mutant polymerase comprising one or more mutations.

12. The composition of claim 6, wherein the second polynucleotide is covalently attached to the surface of a bead.

13. The composition of claim 6, further comprising a population of identical ssDNA templates covalently linked to the surface.

14. The composition of claim 6, wherein the Bst DNA polymerase is a mutant polymerase comprising one or more mutations.

15. The composition of claim 13, further comprising a sequencing primer hybridized to a ssDNA template.

* * * * *

SEQUENCE LISTING

<160> NUMBER OF SEQ ID NOS: 2

<210> SEQ ID NO 1
<211> LENGTH: 581
<212> TYPE: PRT
<213> ORGANISM: Artificial Sequence
<220> FEATURE:
<223> OTHER INFORMATION: Synthetic amino acid

<400> SEQUENCE: 1

```
Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
            195                 200                 205

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
            275                 280                 285

Gln Ser Thr Tyr Ile Glu Gly Leu Leu Lys Val Val Arg Pro Asp Thr
290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
            355                 360                 365

His Ile Ala Glu Asp Asp Asn Leu Met Glu Ala Phe Arg Arg Asp Leu
370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415
```

```
Ile Val Tyr Gly Ile Ser Asp Tyr Gly Leu Ala Gln Asn Leu Asn Ile
                420             425                 430

Ser Arg Lys Glu Ala Ala Glu Phe Ile Glu Arg Tyr Phe Gln Ser Phe
            435                 440                 445

Pro Gly Val Lys Arg Tyr Met Glu Asn Ile Val Gln Glu Ala Lys Gln
            450                 455                 460

Lys Gly Tyr Val Thr Thr Leu Leu His Arg Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
            515                 520                 525

Leu Leu Leu Gln Val His Asp Glu Leu Ile Leu Glu Ala Pro Lys Glu
            530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
                580

<210> SEQ ID NO 2
<211> LENGTH: 49
<212> TYPE: DNA
<213> ORGANISM: Artificial Sequence
<220> FEATURE:
<223> OTHER INFORMATION: Synthetic DNA

<400> SEQUENCE: 2
aaaaaaaaaa aaaaaaaaaa gactgccaag gcacacaggg gataggaaa            49
```